United States Patent [19]

McGovern et al.

[11] Patent Number: 4,681,573
[45] Date of Patent: Jul. 21, 1987

[54] FEMININE URINARY DEVICE

[75] Inventors: Lore H. McGovern, Nashua, N.H.; Alix A. Moore, Santa Anna, Calif.

[73] Assignee: Aplex Corporation, San Mateo, Calif.

[21] Appl. No.: 792,517

[22] Filed: Oct. 29, 1985

[51] Int. Cl.⁴ .............................................. A61F 5/44
[52] U.S. Cl. ..................................... 604/329; 4/144.3
[58] Field of Search ............... 604/329, 330; 128/761; D24/51, 57; 4/144.1–144.4; 229/DIG. 4, 41 B

[56] References Cited

U.S. PATENT DOCUMENTS

| | | | |
|---|---|---|---|
| 2,685,399 | 8/1954 | Crosby | 229/22 |
| 2,878,486 | 3/1959 | Bartlett et al. | 4/144.4 |
| 3,099,017 | 7/1963 | Sullivan | 4/110 |
| 3,535,714 | 10/1970 | Bjork | 4/112 |
| 3,572,318 | 3/1971 | Garland | 4/144.3 |
| 3,680,543 | 8/1972 | Cox | 128/761 |
| 3,731,869 | 5/1973 | Griffen | 229/22 |
| 3,899,123 | 8/1975 | Stollberg | 229/DIG. 4 |
| 4,023,216 | 5/1977 | Li | 604/329 |
| 4,608,046 | 8/1986 | Towfigh | 604/329 |

Primary Examiner—C. Fred Rosenbaum
Assistant Examiner—J. L. Kruter
Attorney, Agent, or Firm—Fliesler, Dubb, Meyer & Lovejoy

[57] ABSTRACT

An oblique conical like urinary device for a standing female to direct a stream of urine a comfortable distance away from the body made of a temporarily fluid resistant material. The device may be erected from a flat blank which may be curved or creased or folded and in some instances sealed. Some embodiments of the device also include outwardly extending flaps on the rear edges and handles projecting from the top of the device.

5 Claims, 7 Drawing Figures

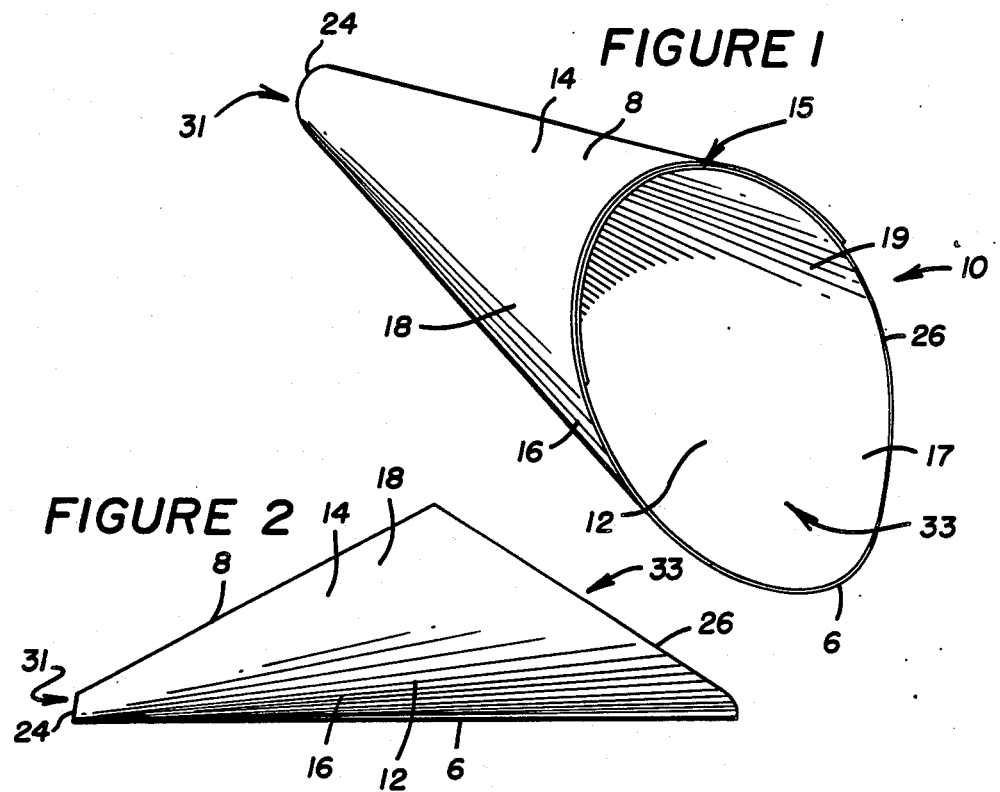
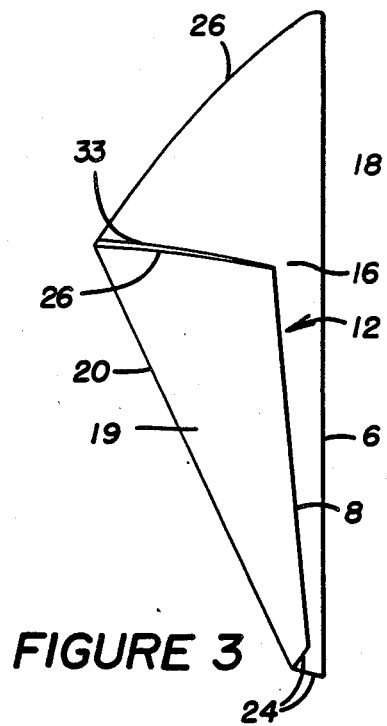

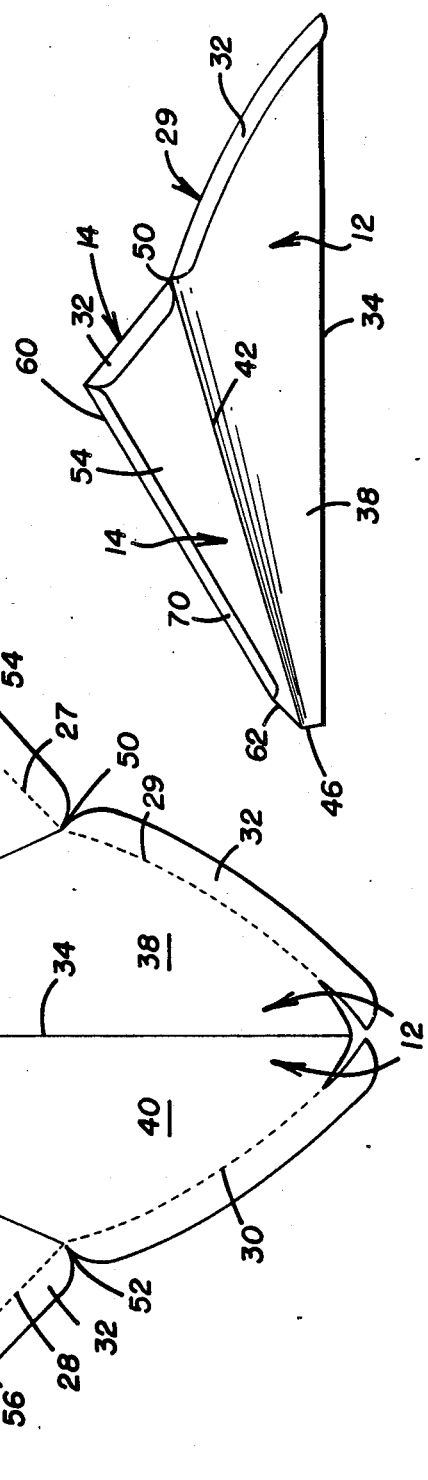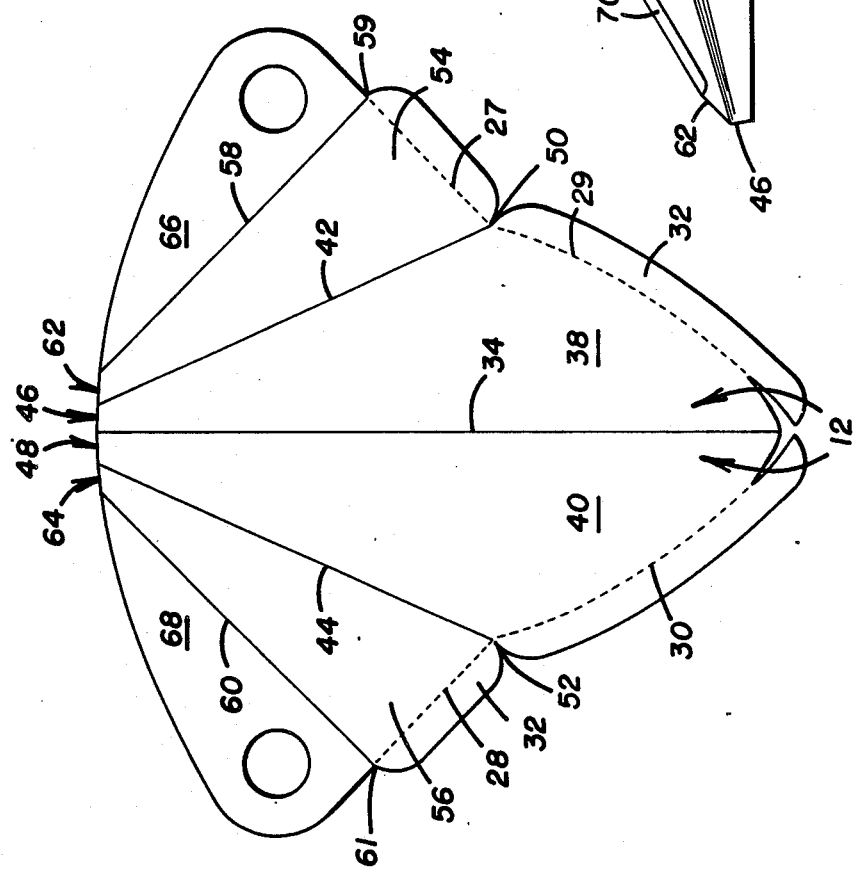

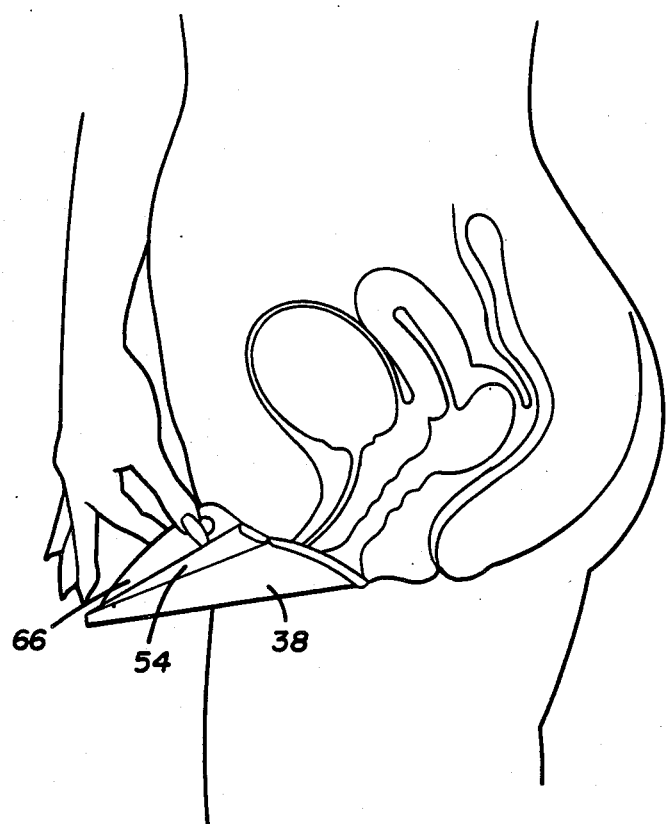
FIGURE 6
FIGURE 7
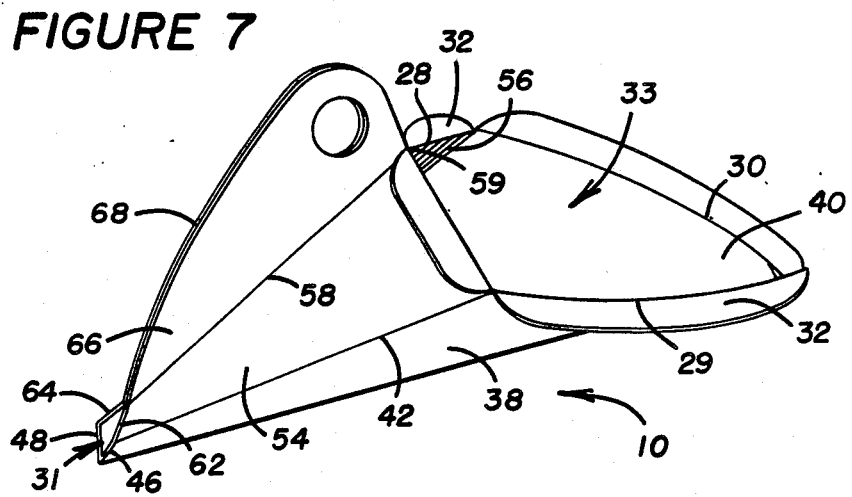

FEMININE URINARY DEVICE

BACKGROUND OF THE INVENTION

1. Field of the Invention

This invention relates to a feminine urinary device and more particularly to an improved fitting and easier to use urinary device for a standing female.

2. Background Art

On account of the female anatomical structure, women and girls often experience difficulty and possible embarrassment and discomfort if they attempt to urinate from a standing position. Certain devices such as those disclosed in U.S. Pat. Nos. 4,023,216 and 3,613,122, have been offered as solutions to this long-standing problem. The device disclosed in U.S. Pat. No. 4,023,216 is open at the top and must be positioned carefully to cover the opening of the urinary tract. To use the device in U.S. Pat. No. 3,613,122, a woman must first spread the labia with the fingers of one hand and then also carefully position the opening of the device in regard to the opening of the urinary tract. These devices therefore require a learning process and continued skill and precision in handling for proper usage.

SUMMARY OF THE INVENTION

The present invention is designed to overcome such problems. One aspect of the invention is to provide a uninary device for a standing female made of an at least temporarily fluid-resistant material for surrounding and channeling but not otherwise interrupting the urine stream of a female and for directing that uninterrupted stream through open space a comfortable distance away from the front of the female. The device comprises during use, an oblique conical like form having an elongated bottom portion having a bottom and two bottom side walls with the bottom side walls having front and rear edges, a top portion integral with but shorter than the bottom portion with the top portion having a downwardly forwardly slanting top and two top side walls having front and rear edges, a narrow front opening formed by the front edges of the top and bottom side walls and an ovate like diagonally downwardly, backwardly slanting rear opening formed by the rear edges of the top and bottom walls and shaped so as to surround the outside of the labia major.

A second aspect of the invention is a collapsible, disposable urinary device for a standing female. The device is erected substantially from a curvilinear creased or scored blank of a plaitable or foldable at least temporarily fluid resistant material into an oblique conical like form for surrounding and channeling but not otherwise interrupting the urine-stream of the female and for directing the stream through open space a comfortable distance away from the front of the female. The form comprises during use:

a bottom having a bottom edge and two substantially identical bottom walls continuous with and extending upwardly and outwardly from both sides of the bottom edge, with the bottom walls each having a downwardly forwardly slanting upper edge, a front edge and a rear edge. The rear edge and upper edge of each bottom wall converge at an apex. Each rear edge slopes diagonally downwardly and backwardly from the apex.

The form also comprises during use, a top having two substantially identical top walls. Each top wall is integral with the upper edge of the bottom wall and has a downwardly forwardly slanting top edge, a front edge and a rear edge with the rear edge and the top edge converging at an apex. Each top wall begins at a corresponding bottom wall apex and is continuous with the upper edge of the corresponding bottom wall. The top walls extend upwardly and inwardly from the upper edges of the bottom walls with the top wall top edges converging towards a vertical plane which intersects the bottom edge.

In addition, the form has two substantially identical handles. Each handle begins at the corresponding apex of a top wall and is continuous with the upper edge of the top wall. The handles are substantially congruently joined substantially within the vertical plane.

In addition the device comprises during use, a front discharge opening formed substantially by the front edges of the top and bottom walls and a diagonally, downwardly, backwardly slanting rear opening formed substantially by the rear edges of the top and bottom walls with the rear opening shaped so as to surround the labia major of the female.

A third aspect of the invention is a collapsible, disposable urinary device for a standing female. The device is erected substantially from a curvilinear creased or scored blank of a plaitable or foldable at least temporarily fluid resistant material into an oblique conical like form for surrounding and channeling but not otherwise interrupting the urine-stream of said female and for directing the stream through open space a comfortable distance away from the front of the female. The form comprises during use:

a bottom having a bottom edge and two substantially identical bottom walls continuous with and extending upwardly and outwardly from both sides of the bottom edge, with the bottom walls each having a downwardly forwardly slanting upper edge, a front edge and a rear edge. The rear edge and upper edge of each bottom wall converging at an apex. Each rear edge slopes diagonally downward and backward from the apex.

The form also comprises during use, a top having two top walls. Each top wall is integral with the upper edge of the bottom wall and has a downwardly forwardly slanting top edge, a front edge and a rear edge with the rear edge and top edge converging at an apex with one of the top edges having a closing means. Each top wall begins at a corresponding bottom wall apex and is continuous with the upper edge of the corresponding bottom wall. The top walls extend upwardly and inwardly from the upper edges of the bottom walls with the top walls being joined by the closing means.

In addition the device comprises during use, a front discharge opening formed substantially by the front edges of the top and bottom walls and a diagonally, downwardly, backwardly slanting rear opening formed substantially by the rear edges of the top and bottom walls with the rear opening shaped so as to surround the labia major.

A forth aspect of the invention is to provide the rear opening or rear edges of the above described device with outwardly extending flaps.

Still another aspect of the invention is to make the above described devices from flushable and biodegradable materials.

Other aspects and advantages of the invention are discussed further in the following detailed description of the preferred embodiments in conjunction with the accompanied drawings which show the various embodiments.

DESCRIPTION OF THE DRAWINGS

FIG. 1 is an isometric view of the device in its erected configuration.

FIG. 2 is a side elevational view of the device.

FIG. 3 is a side view of the collapsed device folded along top, bottom and side creasing lines.

FIG. 4 is a side elevational view of a second embodiment of the device.

FIG. 5 is a plan view of the blank from which a third embodiment of the device is formed.

FIG. 6 is a fragmentary sectional view showing the device in FIG. 5 in relation to the body during urination.

FIG. 7 is a perspective view of the erected device of FIG. 5 in a non-use position.

DETAILED DESCRIPTION OF THE INVENTION

Referring particularly now to FIGS. 1-3, there is seen a collapsible, foldable, disposable, flushable and biodegradable device 10 having a non-reinforced elongated bottom portion 12 and a top portion 14. The device 10 in FIGS. 1 and 2 may also be made from a non-disposable, non-flushable, non-biodegradable, non-collapsible or non-foldable material. The device 10 in FIGS. 1 and 2 may also be made from a pliable resilient material such as certain types of plastics. The device 10 is made from an at least temporarily fluid resistant material such as certain types of papers or light cardboard. The bottom portion 12 has a bottom left side wall 16, a bottom right side wall 17 and a bottom 6. The entire device 10 is designed to act like a funnel with the bottom portion 12 acting as a channel for the urine. The top portion 14 has a top left side wall 18, a top right side wall 19 and a top 8. The top portion 14 slants downwardly and forwardly and is integral with the bottom portion 12. Unless the device has been collapsed from top to bottom (not shown), giving side creasing lines 20 (see FIG. 3), there is no definitive demarcation between the top 14 and bottom 12 portions or between top left side wall 18 and bottom left side wall 16 or between top right side wall 19 and bottom right side wall 17. However, the device 10 like other conical shapes is formed by line segments 21. Whether or not line segments 21 are actually depicted, they always exist as a function of the geometry of conical shapes. The bottom most line segment of the device 10 is the same as the bottom 6 and is straight and uninterrupted. Both the bottom portion 12 and the top portion 14 have front 24 and rear 26 edges. The rear edges 26 lie in the same plane as the corresponding side walls 16, 17, 18, 19, converge at the bottom line segment 6 and define a rear opening 33 while the front edges 24 define a front opening 31 (see also FIG. 7). As shown in FIGS. 1 and 2, the front opening 31 is quite narrow while the rear opening 33 (see especially FIG. 1) is much larger and wider. When the device is in position for use the rear opening 33 is elongated, ovate like and slants diagonally backwardly and downwardly.

The device 10 in FIGS. 1-3 is constructed from a blank, not shown, wherein the portion of the blank that forms the top left side wall 18 and part of top right side wall 19 overlaps the portion of the blank that forms top wall 19 and part of top wall 18. The two overlapping areas are joined by an adhesive or glue to form a closing means 15.

Unless the device 10 is also collapsed from right to left, there is no definitive demarcation between the bottom right side wall 17 or between the top left side wall 18 and the top right side wall 19.

If the device 10 has been collapsed from left to right only (not shown) the usable form may be erected from the collapsed device by placing ones fingers between the inside of the rear opening 33, so that rear opening 33 is at least slightly opened, and pushing the side walls 16, 17 or 18, 19 outward from the inside of the device. Once the rear opening 33 is slightly open, the usable form may also be erected by simultaneously pushing the portion partially downward and the bottom portion partially upward from the outside. In the instance where the device is collapsed only from top to bottom along its side creasing lines 20 (not shown), the device is erected into its position for use by again placing fingers inside the rear opening 33 and pushing the top portion 14 partially upward and the bottom portion 12 partially downward. When the device is collapsed from left to right and folded as in FIG. 3, the device is first unfolded along the side creasing lines 20 to resemble a figure that would look like FIG. 2 if FIG. 2 had creasing lines and may then be pushed outward along the side creasing lines 20. If the device 10 is made from a non-collapsible material it is already in the usable form. When the device is held in its use position, so that the rear opening surrounds the labia major, and is creased or made of a pliable material, it may be further adjusted to fit more comfortably by applying a slight inward pressure along the outside of the side creasing lines 20 or the outside of the top 8 may be pushed slightly downward while the bottom 6 is pushed slightly upward. This may be done by holding the device with only one hand. During use, the bottom portion 12 is held from the outside preferably in a very slight downwardly forwardly directed position. The bottom portion 12 may also be held horizontally at a right angle but never in a position where the inside of the bottom 6 makes an acute angle with the upright axis of the body. Any urine remaining on the body after use may be removed by moving the device 10 forward along the vulva so as to wipe away the traces of urine with the back of the rear edges 26. Any residual remaining urine may also be removed by toilet paper or the like, two or three tissues of which may be easily packaged with each device.

Referring now to FIGS. 4-7, which show other embodiments of the device wherein the blank used to form the device has been prescored or creased and the previouslydescribed rear edges 26 have been converted to definitive top left and right (with regard to the body during use) rear edges 27, 28 and bottom left and right rear edges 29, 30 which are connected to curved flaps 32. The rear most portion of the flaps 32 of the rear edges are detached from the rear edges 29 and 30 as shown in FIGS. 5 and 7. The bottom portion 12 now has a definite bottom edge 34 and two tapering bottom walls 38 and 40. These bottom walls 38, 40 extend upwardly and outwardly from both sides of the bottom edge 34 during use. Each bottom wall has an upper edge 42, 44, and a front edge 46, 48. The bottom rear edges 29, 30 are elongated in comparison to the front edges 48 and 46. The upper edges 42, 44 and the rear edges 29, 30 converge at apexes 50 and 52. The top and bottom rear edges 27, 28, 29, 30 each lie in the same plane as each corresponding top and bottom wall 54, 56, 38, 40 and the rear edges converge at the bottom edge 40. The device 10 has a top portion 14. The top portion 14 has tapering top walls 54 and 56 having top edges 58 and 60 and front edges 62, 64 respectively. In the embodiment shown in FIG. 4 the top edge 60 is connected to a closing means 70 such as a tab which is held to top wall 54 by adhesive or the like joining top walls 54 and 56 during use. The embodiment depicted in FIG. 4 is used as a urinary device in the same manner as the manner described for the embodiment depicted in FIG. 3. In the embodiment depicted in FIGS. 5–7, handles 66 and 68 extend respectively from the upper edges 58 and 60. Except for the presence of closing means 15 instead of handles 66, 68 the blank for erecting the embodiment in FIG. 4 is identical to the blank shown in FIG. 5. The device 10 in FIG. 4 may also have handles attached to its top portion 14 but these are not shown.

During use the device 10 (in FIGS. 5–7) is held by clasping the handles 66 and 68 congruently together with the rear most portion of the bottom rear edges 29, 30 extending preferably beyond the rear most portion of the outside of the labia major. As shown in FIG. 6 the device is held slightly forwardly downward in relation to the body and the urine stream is discharged forwardly and downwardly a comfortable distance away from the body through the opening 31 composed of the front edges 46, 48, 62, 64. Gravitional forces acting on the urine stream direct it downward. The flaps 32 are directed outwardly (i.e. substantially perpendicular from the walls 38, 40, 54 and 56. and the area between the rear edges 27, 28, 29 and 30 and the flaps 32 are perforated.) The flaps 32 alleviate discomfort which might be caused by contact with the rear edges 29, 30, 27, 28. While the rear edges 27, 28, 29, 30 surround the outside of the labia major and usually touch is not necessary that they directly touch the labia major. It can be observed that the walls 38, 40, 54, 56 are relatively long and that the bottom walls 38 and 40 are preferably about one and a half times as long as the top walls 54 and 56.

Unlike the prior art, the present invention is easy to use and is less likely to involve accidental leaking or spillage since the rear opening is designed to fit around the outside of the labia major during use. This fit is natural and automatically comfortable in its correct usage position and it is therefore unnecessary as with the devices described in the prior art to carefully place the rear opening of the device in relation to the opening of the urinary tract. Therefore, no learning process or skill in handling is required for correct usage of the present invention. The device may be held adequately with one hand during use leaving the other hand free. Also because the rear opening automatically surrounds the labia major, a woman does not have to touch the vulva with her fingers to properly place the device during correct use.

If the material of the device is foldable, pliable or bendable, the device may be further adjusted to custom fit the area around the labia major between the legs by only applying a small amount of pressure with the holding hand simultaneously to the outside of the top portion and bottom portion or to the side walls.

If the device is foldable, or plaitable the top walls are folded back on top of the bottom walls making the device extremely compact and portable so as to easily fit inside a backpack, purse or even a pocket. If the plaitable device has handles it is just as portable since these handles can be folded back over or under the top walls.

The device that has handles has a further advantage in that by using the handles the warm sensation from the urine stream, which may be felt when the device is held from the bottom and which some women find discomforting, may be avoided.

Although the foregoing invention has been described in some detail by way of illustrations, it should be recognized that certain changes and modification may be practiced within the scope of the appended claims.

What is claimed is:

1. A collapsible, disposable urinary device for a standing female erected substantially from a curvilinear creased or scored blank of a plaitable or foldable at least temporarily fluid resistant material into an oblique conical like form for surrounding and channeling but not otherwise interrupting the urine-stream of said female and for directing said stream through open space a comfortable distance away from the front of said female; said form comprising during use:

a bottom having a bottom edge and two substantially identical bottom walls continuous with and extending upwardly and outwardly from both sides of said bottom edge, said bottom walls each having a downwardly, forwardly slanting upper edge, a front edge and a rear edge, said rear edge and said upper edge of each bottom wall converging at an apex with each said rear edge sloping diagonally downwardly and backwardly from said apex and each said rear edge having an outwardly extending flap with a front and rear portion, said rear portion being partially detached from said rear edge;

a top having two substantially identical top walls, each top wall being integral with said upper edge of said bottom wall, each said top wall having a downwardly forwardly slanting top edge, a front edge and a rear edge with said rear edge and said top edge converging at an apex and each said rear edge having an outwardly extending flap with a front and rear portion, each said top wall beginning at the corresponding bottom wall apex and being continuous with the upper edge of said bottom wall, said top walls extending upwardly and inwardly from said upper edges of said bottom walls with said top wall top edges converging towards a vertical plane which intersects said bottom edge;

two substantially identical handles, each handle beginning at the corresponding apex of a top wall and being continuous with the upper edge of said top wall, said handles being substantially congruently joined substantially within said vertical plane;

a front discharge opening formed substantially by the front edges of the top and bottom walls; and a diagonally, downwardly, backwardly slanting rear opening formed substantially by the rear edges of the top and bottom walls said rear opening shaped so as to surround the labia major of said female.

2. A collapsible, disposable urinary device for a standing female erected substantially from a curvilinear creased or scored blank of a plaitable or foldable at least temporarily fluid resistant material into an oblique conical like form for surrounding and channeling but not otherwise interrupting the urine-stream of said female and for directing said stream through open space a comfortable distance away from the front of said female; said form comprising during use:

a bottom having a bottom edge and two substantially identical bottom walls continuous with and extending upwardly and outwardly from both sides of said bottom edge, said bottom walls each having a downwardly forwardly slanting upper edge, a front edge and a rear edge, said rear edge and said upper edge of each bottom wall converging at an apex with each said rear edge sloping downwardly and backwardly from said apex and each said rear edge having an outwardly extending curved flap interconnected to said rear edge by perforations;

a top having two top walls, each wall integral with said upper edge of said bottom wall and having a downwardly forwardly slanting top edge, a front edge and a rear edge with said rear edge and said top edge converging at an apex with one of the top edges having a closing means and each said rear edge having an outwardly extending curved flap interconnected to said rear edge by perforations, each said top wall beginning at the corresponding bottom wall apex and being continuous with the upper edge of said bottom wall, said top walls extending upwardly and inwardly from said upper edges of said bottom walls with said top walls being joined by said closing means;

a front discharge opening formed substantially by the front edges of the top and bottom walls; and a diagonally, downwardly, backwardly slanting rear opening formed substantially by the rear edges of the top and bottom walls said rear opening shaped so as to surround the labia major of said female.

3. A collapsible, disposable urinary device for a standing female erected substantially from a curvilinear creased or scored blank of a plaitable or foldable at least temporarily fluid resistant material into an oblique conical like form for surrounding and channeling but not otherwise interrupting the urine-stream of said female and for directing said stream through open space a comfortable distance away from the front of said female; said form comprising during use:

a bottom having a bottom edge and two substantially identical bottom walls continuous with and extending upwardly and outwardly from both sides of said bottom edge, said bottom walls each having a downwardly forwardly slanting upper edge, a front edge and a rear edge, said rear edge and said upper edge of each bottom wall converging at an apex with each said rear edge sloping downwardly and backwardly from said apex and each said rear edge having an outwardly extending curved flap with a front and rear portion said rear portion of said flap being partially detached from said rear edge;

a top having two top walls, each wall integral with said upper edge of said bottom wall and having a downwardly forwardly slanting top edge, a front edge and a rear edge with said rear edge and said top edge converging at an apex with one of said top edges having a closing means and each said rear edge having an outwardly extending flap with a front and rear portion, each said top wall beginning at the corresponding bottom wall apex and being continuous with the upper edge of said bottom wall, said top walls extending upwardly and inwardly from said upper edges of said bottom walls with said top walls being joined by said closing means;

a front discharge opening formed substantially by the front edges of the top and bottom walls; and a diagonally, downwardly, backwardly slanting rear opening formed substantially by the rear edges of the top and bottom walls with said rear opening shaped so as to surround the labia major of said female.

4. A urinary device for a standing female made of an at least temporarily fluid-resistant material for surrounding and channeling but not otherwise interrupting the urine stream of said female and for directing said uninterrupted stream through open space a comfortable distance away from the front of said female, said device comprising during use:

an oblique conical like form having:

an elongated bottom portion having a straight uninterrupted bottom line segment and two bottom side walls, said bottom side walls having corresponding front and rear edges with each said rear edge lying in the same plane as each corresponding bottom side wall and said rear edges converging at said bottom line segment;

a top portion integral with but shorter than said bottom portion, said top portion having a downwardly forwardly slanting top and two top side walls having front and rear edges;

a narrow front opening formed by said front edges of said top and bottom side walls; and an ovate like, diagonally, downwardly, backwardly slanting rear opening shaped so as to surround the outside of the labia major of said female and formed by said rear edges of said top and bottom walls, said rear opening having one or more flaps extending outwardly from said rear edges with perforations between the rear opening and the flaps, said flaps being substantially perpendicular from said corresponding sidewalls.

5. A collapsible, disposable urinary device for a standing female erected substantially from a curvilinear creased or scored blank of a plaitable or foldable at least temporarily fluid resistant material into an oblique conical like form for surrounding and channeling but not otherwise interrupting the urine-stream of said female and for directing said stream through open space a commfortable distance away from the front of said female; said form comprising during use:

a bottom having a bottom edge and two substantially identical bottom walls continuous with and extending upwardly and outwardly from both sides of said bottom edge, said bottom walls each having a correspondingly downwardly forwardly slanting upper edge, a front edge and a rear edge, said rear edge and said upper edge of each bottom wall converging at an apex and each said rear edge sloping diagonally downwardly and backwardly from said apex;

a top having two substantially identical top walls, each top wall being integral with said upper edge of said bottom wall, each said top wall having a correspondingly downwardly forwardly slanting top edge, a front edge and a rear edge with said rear edge and said top edge converging at an apex, each said top wall beginning at the corresponding bottom wall apex and being continuous with the upper edge of said bottom wall, said top walls extending upwardly and inwardly from said upper edges of said bottom walls with said top wall top edges converging towards a vertical plane which intersects said bottom edge;

two substantially identical handles, each handle beginning at the corresponding apex of a top wall and being continuous with the upper edge of said top wall, said handles being substantially congruently joined substantially within said vertical plane;

a front discharge opening formed substantially by the front edges of the top and bottom walls; and a diagonally, downwardly, backwardly slanting rear opening shaped so as to surround the labia major of said female and formed substantially by the rear edges of the top and bottom walls said rear edges having outwardly extending flaps with perforations interrupting the rear edges and the flaps, said flaps being substantially perpendicular to said corresponding walls.

* * * * *